US00PP16238P2

(12) United States Plant Patent
Amorao et al.

(10) Patent No.: US PP16,238 P2
(45) Date of Patent: Feb. 7, 2006

(54) STRAWBERRY PLANT NAMED 'DRISCOLL EL DORADO'

(50) Latin Name: *Fragaria×ananassa*
Varietal Denomination: Driscoll El Dorado

(75) Inventors: Amado Q. Amorao, Camarillo, CA (US); Michael Ferguson, Moorpark, CA (US); Arnoldo Solis, Jr., Oxnard, CA (US)

(73) Assignee: Driscoll Strawberry Associates, Inc.

( * ) Notice: Subject to any disclaimer, the term of this patent is extended or adjusted under 35 U.S.C. 154(b) by 88 days.

(21) Appl. No.: 10/957,845

(22) Filed: Oct. 4, 2004

(51) Int. Cl.
*A01H 5/00* (2006.01)

(52) U.S. Cl. ..... Plt./209

(58) Field of Classification Search ..... Plt./209
See application file for complete search history.

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll El Dorado.' The variety is similar to the varieties 'Camarosa' and 'Ventana.' The variety is distinguished from 'Camarosa' and 'Ventana,' in particular, by a greater number of teeth per Terminal Leaflet, fewer achenes per fruit, a rounded shape of the base of terminal leaflets, a rounded shape of the teeth terminal leaflets, sparse to medium petiole pubescence, larger size of calyx in relation to fruit on secondary fruit, and a medium sized hollow center of fruit.

5 Drawing Sheets

1. Latin name of the genus and species of the plant claimed: The variety is botanically identified as *Fragaria× ananassa.*

1.1 Variety denomination: The strawberry variety denomination is 'Driscoll El Dorado'.

2. BACKGROUND OF THE INVENTION

The new variety originated as a result of a controlled cross between the strawberry plants '62C131' (unpatented) and 'Camarosa' (U.S. Plant Pat. No. 8,708) in an ongoing breeding program, and was discovered as a seedling in Ventura County, Calif. in 1999. The original seedling of the new cultivar was asexually propagated by stolons in a Nursery in Shasta County, Calif. Propagules were transplanted to a controlled breeding plot in Ventura County, Calif., where the variety was identified and selected for further evaluation. 'Driscoll El Dorado' was subsequently asexually propagated and underwent further testing in Ventura County, Calif. for five years. This propagation and testing has demonstrated that the combination of traits disclosed herein which characterize the new variety are fixed and retained true to type through successive generations of asexual reproduction.

3. SUMMARY OF THE INVENTION

The present invention relates to a new and distinct variety of strawberry named 'Driscoll El Dorado.' The variety is botanically identified as *Fragaria×ananassa.* The new variety is distinguished from other varieties by a number of characteristics as set forth in Tables 1–4.

4. COMPARISON TO SIMILAR VARIETIES

The varieties which we believe to be similar to 'Driscoll El Dorado' from those known to us are 'Camarosa' (U.S. Plant Pat. No. 8,708) and 'Ventana' (U.S. Plant Pat. No. 13,469). There are several characteristics of the new variety that are different from, or not possessed by 'Camarosa' and 'Ventana'. For example, the new variety has a greater number of teeth per Terminal Leaflet, fewer achenes per fruit, a rounded shape of the base of terminal leaflets, a rounded shape of the teeth terminal leaflets, sparse to medium petiole pubescence, larger size of calyx in relation to fruit on secondary fruit, and a medium sized hollow center of fruit.

Maternal Parent '62C313' was not available for side by side comparison with 'Driscoll El Dorado'. 'Driscoll El Dorado' is distinguished from its maternal parent '62C313' by its earlier date of harvest commencement, firmer fruit flesh, and less creasing on the fruit. 'Driscoll El Dorado' is distinguished from its paternal parent 'Camarosa' as indicated in Tables 1–4.

5. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

6. DESCRIPTION OF THE NEW VARIETY

Figure 1:
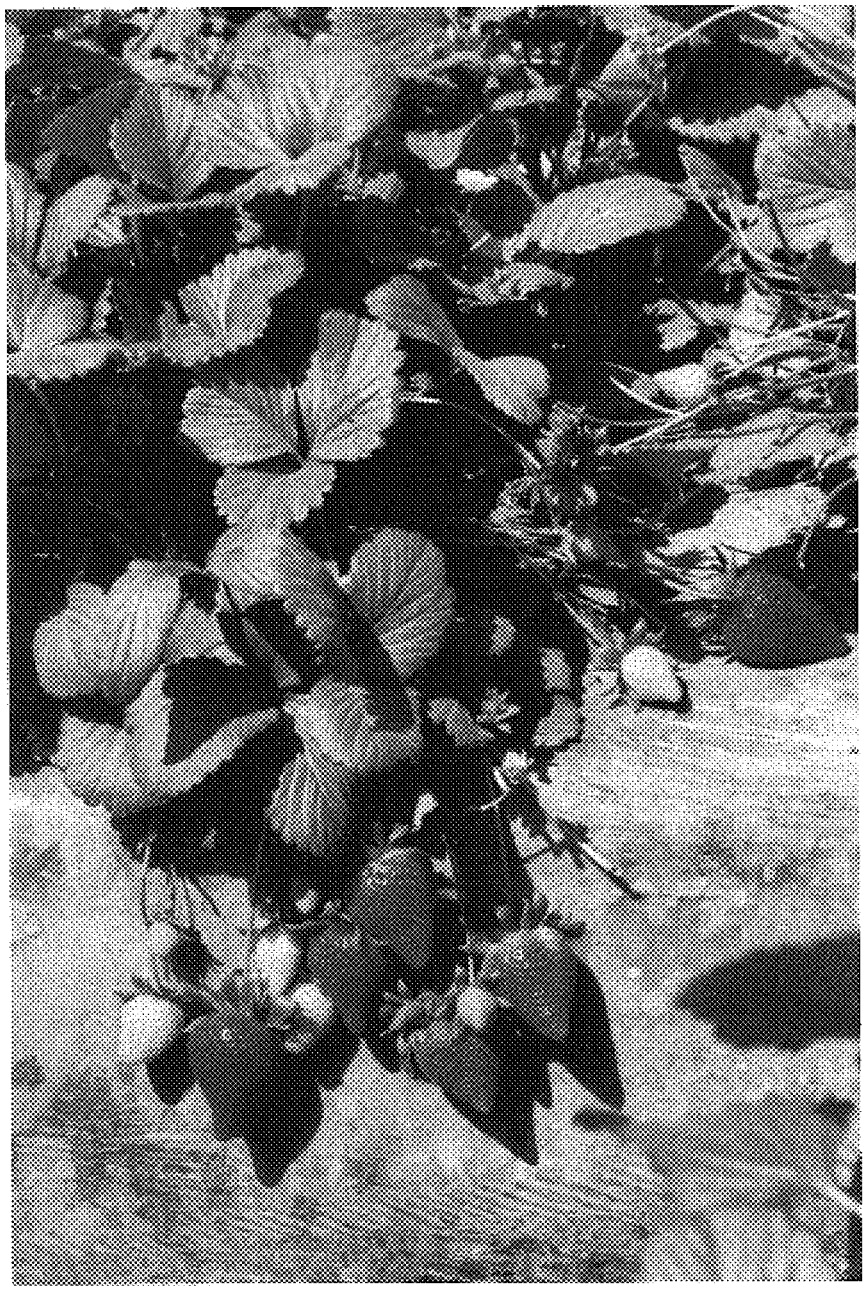
FIG. 1 shows the whole the plant.
Figure 2:
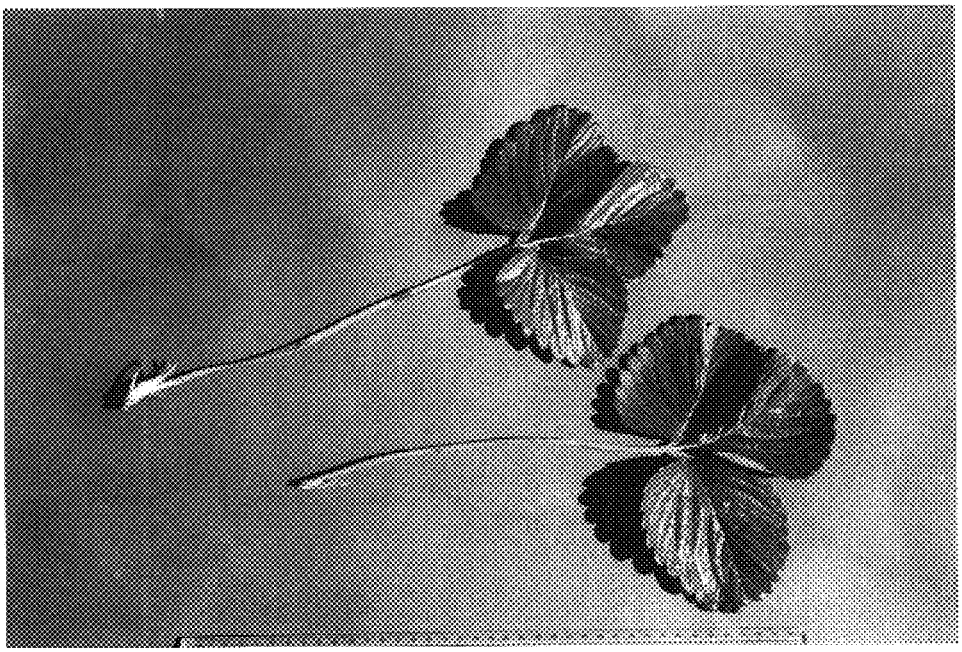
FIG. 2 shows the upper side of the leaves of the plant.
Figure 3:
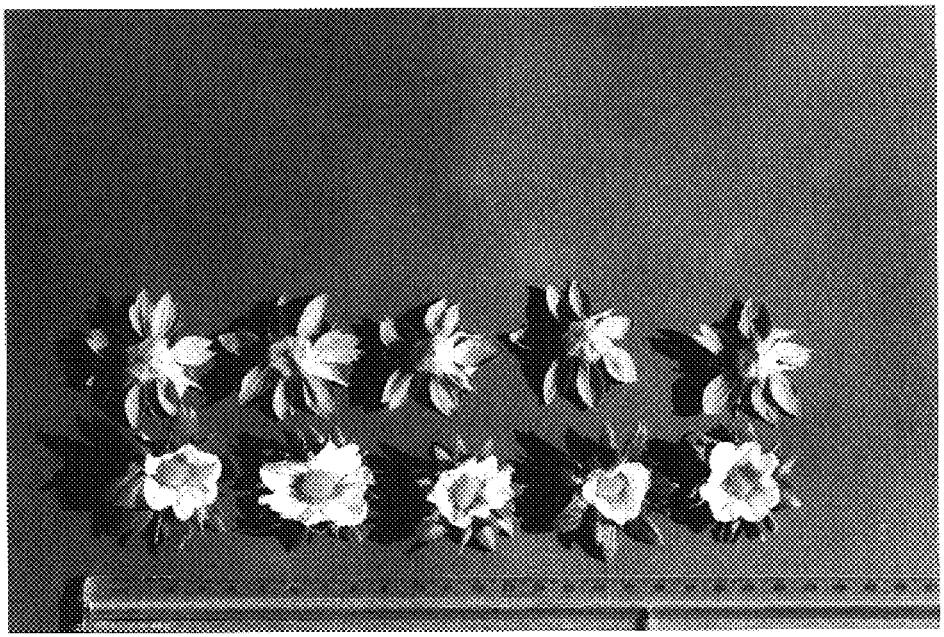
FIG. 3 shows the underside and upperside of the flowers.
Figure 4:
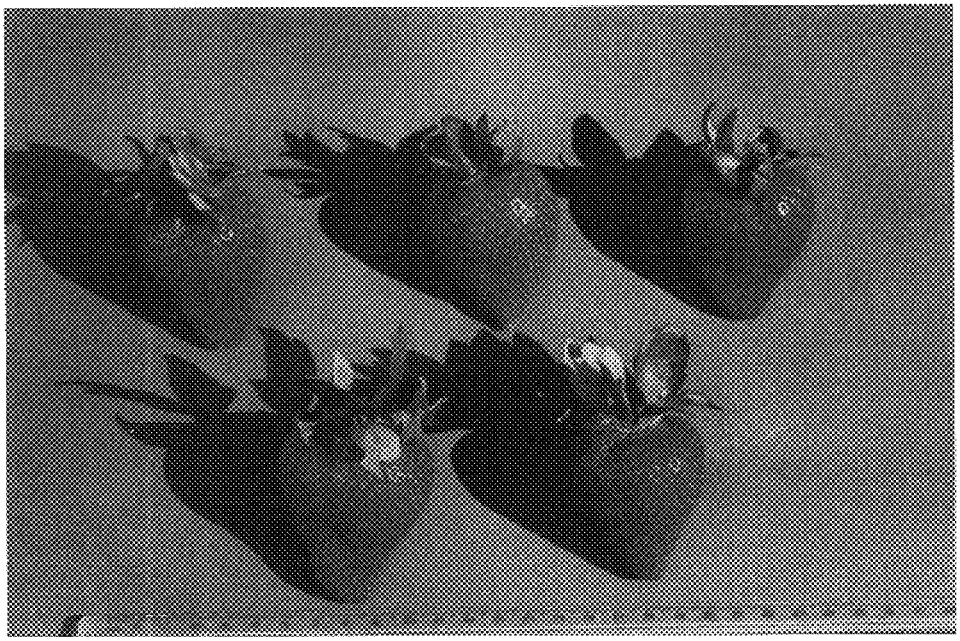
FIG. 4 shows a close-up of the fruit.
Figure 5:
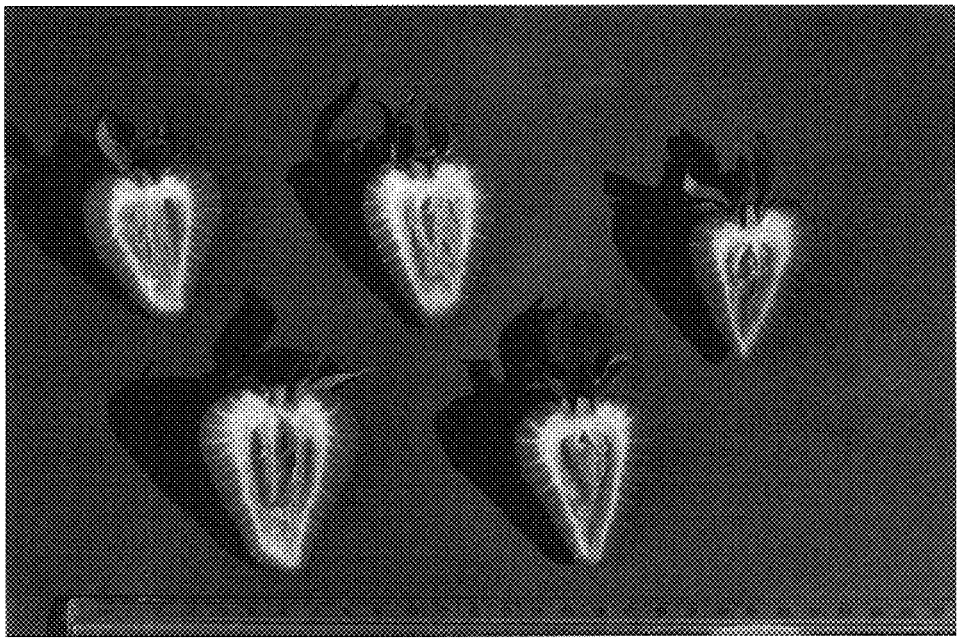
FIG. 5 shows the fruit in longitudinal cross-section.

The following detailed description of the new variety is based upon observations taken of plants and fruit grown in Ventura County, Calif., U.S.A. This description is in accordance with UPOV terminology. Observations of 'Driscoll El Dorado', 'Camarosa' and 'Ventana' were taken in side by side comparison in the 2004 spring season. Plants were grown in raised beds of soil under conditions typical of commercial strawberry production in Southern California. Fruits were harvested twice weekly for yield determination from early January to late May. Measurements of plant, flower, and fruit characteristics were made in April, approximately six months after planting. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

6.1 PROPAGATION

The new variety is principally propagated by way of stolons. Although propagation by stolons is presently preferred, other known methods of propagating strawberry plants may be employed.

6.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on six month old plants. Fruit and flower measurements are an average of both primary and secondary fruit and flowers.

Table 1 provides information on the plant and fruit characteristics of the new variety 'Driscoll El Dorado' compared with characteristics of 'Camarosa' and 'Ventana.' Table 2 provides additional information of the plant and fruit characteristics of the new variety 'Driscoll El Dorado' compared with characteristics of the varieties 'Camarosa' and 'Ventana.' Table 3 provides reactions of the new variety to stresses, pests and diseases compared with reactions of the varieties 'Camarosa' and 'Ventana.' Table 4 provides isozyme characteristics of the new variety as compared to that of the varieties 'Camarosa' and 'Ventana.'

TABLE 1

QUANTITATIVE COMPARISON OF 'DRISCOLL EL DORADO,' 'CAMAROSA,' AND 'VENTANA'

| | 'Driscoll El Dorado' | 'Camarosa' | 'Ventana' |
|---|---|---|---|
| Plant Characteristics | | | |
| Height of Plant (cm) | 24.0 | 30.7 | 24.8 |
| Spread of Plant (cm) | 27.5 | 31.4 | 28.3 |
| Number of Crowns | 5.4 | 8.8 | 5.4 |
| Leaf Characteristics | | | |
| Terminal Leaflet Length (cm) | 7.4 | 7.5 | 7.3 |
| Terminal Leaflet Width (cm) | 6.0 | 6.8 | 5.6 |
| Terminal Leaflet Length/Width Ratio | 1.24 | 1.10 | 1.31 |
| # Teeth/Terminal Leaflet | 20.5 | 18.5 | 18.3 |
| Color of upper side | 139A medium to dark green | 141A medium green | 141A light to medium green |
| Color of under side | 138B light gray green | 138C light gray green | 139C light gray green |
| Petiole Length (cm) | 16.6 | 21.0 | 18.0 |
| Petiole Color | 145B yellow green | 145A yellow green | 145A yellow green |

TABLE 1-continued

QUANTITATIVE COMPARISON OF 'DRISCOLL EL DORADO,' 'CAMAROSA,' AND 'VENTANA'

| | 'Driscoll El Dorado' | 'Camarosa' | 'Ventana' |
|---|---|---|---|
| Petiolule Length (mm) | 7.0 | 12.1 | 5.8 |
| Petiolule Diameter (mm) | 2.0 | 1.8 | 1.8 |
| Petiolule Color | 145B yellow green | 144B yellow green | 145A yellow green |
| Bract Frequency | 0 | 0 | 0 |
| Stipule Length (cm) | 3.49 | 3.30 | 3.52 |
| Stipule Width (cm) | 1.0 | 1.2 | 1.1 |
| Stolon Characteristics | | | |
| Anthocyanin color | 59C | | |
| Diameter at bract (mm) | 2.59 | | |
| Avg. # of Daughter plants (2003 Nursery) | 129 | | |
| Flower Characteristics | | | |
| Petal Length (cm) | 1.24 | 1.13 | 1.25 |
| Petal Width (cm) | 1.24 | 1.11 | 1.32 |
| Petal Length/Width Ratio | 1.00 | 1.02 | 0.95 |
| Flower Diameter (cm) | 2.45 | 2.21 | 2.73 |
| Calyx Diameter (cm) | 4.10 | 4.23 | 3.66 |
| Sepal Length (mm) | 18.05 | 17.92 | 15.31 |
| Sepal Width (cm) | 7.61 | 7.72 | 6.00 |
| Petal Color | 155C white | 155C white | 155C white |
| Receptical Color | 7A yellow green | 7A yellow green | 7A yellow green |
| Anther Color | 14B yellow | 14B yellow | 14B yellow |
| Fruiting Truss Length (cm) | 24.5 | 25.2 | 24.2 |
| Fruit Characteristics | | | |
| Fruit Length (cm) | 4.5 | 4.7 | 4.4 |
| Fruit Width (cm) | 4.1 | 3.5 | 3.6 |
| Fruit Length/Width Ratio | 1.10 | 1.33 | 1.21 |
| Average Berry Weight (g) | 22.8 | 21.3 | 24.4 |
| External Color | 46A dark red | 46A dark red | 44A red |
| Internal Color | 42A orange red | 43A medium red | 42B orange red |
| Achene Coloration | 12B to 184A yellow to grayed red | 11A to 179B yellow to grayed red | 11A to 176B yellow to grayed red |
| Achenes per berry | 247 | 310 | 319 |
| Achene weight (g) | 0.00049 | 0.00055 | 0.00042 |
| 2004 Marketable Yield (g/plant) | 830 | 766 | 1,016 |

TABLE 2

QUALITATIVE COMPARISON OF 'DRISCOLL EL DORADO,' 'CAMAROSA,' AND 'VENTANA'

| | 'Driscoll El Dorado' | 'Camarosa' | 'Ventana' |
|---|---|---|---|
| Plant | | | |
| Habit | globose | globose | flat globose |
| Canopy Density | dense | dense | dense |
| Vigor | strong | strong | medium to strong |
| Leaf | | | |
| Shape in cross section | slightly concave | concave | concave |
| Interveinal blistering | weak | medium to strong | weak to medium |
| Glossiness | medium | weak to medium | weak to medium |

TABLE 2-continued

QUALITATIVE COMPARISON OF 'DRISCOLL EL DORADO,' 'CAMAROSA,' AND 'VENTANA'

| | 'Driscoll El Dorado' | 'Camarosa' | 'Ventana' |
|---|---|---|---|
| Number of leaflets | three only | three only | occasionally 4 |
| Terminal leaflet margin profile | revolute to flat | revolute to flat | revolute |
| Terminal leaflet shape of base | rounded | obtuse | slightly oblique |
| Terminal leaflet shape of teeth | rounded | obtuse | obtuse |
| Stipule pubescence | sparse | medium | medium |
| Petiole pubescence | sparse to medium | dense | dense |
| Petiole pose of hairs | upwards to outwards | upwards | upwards |
| Stolon | | | |
| Anthocyanin coloration | medium | | |
| Thickness | thin | | |
| Pubescence | medium | | |
| Inflorescence | | | |
| Position relative to foliage | above | level with to above | level with to above |
| Diameter of calyx relative to corolla on secondary flowers | larger | larger | smaller |
| Diameter of inner calyx relative to outer on secondary flowers | smaller to same size | smaller | larger |
| Spacing of petals | overlapping | overlapping, occasionally free | touching to overlapping |
| Fruiting Truss | | | |
| Attitude at first picking | prostrate | prostrate | prostrate |
| Fruit | | | |
| Predominant shape | conical | almost cylindrical | conical to almost cylindrical |
| Difference in shapes between primary and secondary fruits | slight | moderate to marked | slight to moderate |
| Band without achenes | narrow to medium | medium to broad | narrow to medium |
| Unevenness of surface | weak | strong | medium |
| Evenness of color | even | slightly uneven | even |
| Glossiness | strong | strong | strong |
| Insertion of achenes | below surface | below surface | below surface |
| Insertion of calyx | level | set above fruit | level |
| Pose of the calyx segments | spreading to reflexed | spreading to reflexed | spreading |
| Size of calyx in relation to fruit on secondary fruit | larger | same size to smaller | smaller |
| Adherence of calyx | strong | strong | strong |
| Firmness of flesh | firm | firm to extremely firm | extremely firm |
| Evenness of flesh color | slightly uneven | even | slightly uneven |
| Distribution of flesh color | mariginal and central | mariginal and central | mariginal and central |
| Hollow center size | medium | small | small |
| Sweetness | medium | medium | medium |
| Texture when tasted | medium | coarse | coarse |
| Acidity | medium | medium | medium |
| Time of First Flowering in 2003–2004 | Late-November | Late-November | Late-November |
| Harvest Interval in 2004 | Early-January to Late-May | Early-January to Late-May | Early-January to Late-May |

TABLE 2-continued

QUALITATIVE COMPARISON OF 'DRISCOLL EL DORADO,' 'CAMAROSA,' AND 'VENTANA'

| | 'Driscoll El Dorado' | 'Camarosa' | 'Ventana' |
|---|---|---|---|
| Type of Bearing | partially everbearing | partially everbearing | June bearing |

6.3 REACTION TO STRESS, PESTS, AND DISEASE

TABLE 3

REACTIONS TO STRESS PESTS AND DISEASES FOR 'DRISCOLL EL DORADO,' 'CAMAROSA,' AND 'VENTANA'

| | 'Driscoll El Dorado' | 'Camarosa' | 'Ventana' |
|---|---|---|---|
| Reaction to Pests | | | |
| *Tetranychus urticae* | susceptible | moderately resistant | moderately resistant |
| *Lygus hesperus* | susceptible | susceptible | susceptible |
| Reaction To Diseases | | | |
| Botrytis fruit rot | susceptible | | |
| Powdery mildew | moderately resistant | moderately resistant | moderately resistant |
| *Verticillium* wilt | moderately susceptible | | moderately susceptible |
| Strawberry Mottle Virus | moderately resistant | moderately resistant | moderately resistant |
| *Xanthomonas fragariae* | moderately susceptible | | |

6.4 ISOZYME ANALYSIS

In addition to the morphological description above, the new cultivar 'Driscoll El Dorado' has been analyzed to obtain an indication of its genetic makeup to provide further means for identifying the new variety and distinguishing it from other somewhat similar and/or related strawberry varieties. Specifically, leaf samples of 'Driscoll El Dorado', 'Camarosa' and 'Ventana' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterizatin of the three varieties is presented in Table 4, with the letters representing the banding patterns for each enzyme as designated in the above-identified article.

TABLE 4

ISOZYME ANALYSIS FOR 'DRISCOLL EL DORADO,' 'CAMAROSA,' AND 'VENTANA'

| Locus | 'Driscoll El Dorado' | 'Camarosa' | 'Ventana' |
|---|---|---|---|
| PGI | A2 | A2 | A1 |
| LAP | B1 | B3 | B1 |
| PGM | C3 | C1 | C2 |

What is claimed:

1. A new and distinct variety of strawberry plant, substantially as shown and described.

* * * * *